US008029538B2

(12) United States Patent
Burroughs et al.

(10) Patent No.: US 8,029,538 B2
(45) Date of Patent: Oct. 4, 2011

(54) BABY TEETHING/FEEDING DEVICE

(76) Inventors: Dacosta T. Burroughs, Las Vegas, NV (US); Zenaida L. Burroughs, Las Vegas, NV (US)

( * ) Notice: Subject to any disclaimer, the term of this patent is extended or adjusted under 35 U.S.C. 154(b) by 424 days.

(21) Appl. No.: 12/120,010

(22) Filed: May 13, 2008

(65) Prior Publication Data

US 2011/0208241 A1 Aug. 25, 2011

(51) Int. Cl.
*A61B 17/00* (2006.01)
*A61J 9/00* (2006.01)

(52) U.S. Cl. .................................... 606/234; 215/11.1

(58) Field of Classification Search .................. 606/234, 606/236; 215/11.1, 11.2, 11.3, 11.4, 11.5
See application file for complete search history.

(56) References Cited

U.S. PATENT DOCUMENTS 1,518,823 A * 12/1924 Schmidt et al. .............. 215/11.1
1,913,627 A * 6/1933 Epstein ........................ 215/11.1
2,954,030 A * 9/1960 Jozwiak ....................... 215/11.1
3,610,248 A * 10/1971 Davidson ...................... 606/236
4,105,032 A 8/1978 Blomstedt
4,765,037 A * 8/1988 Perry .............................. 24/301
D300,059 S 2/1989 Pier
4,986,751 A * 1/1991 Bergersen ......................... 433/6
5,176,705 A 1/1993 Noble
5,334,218 A * 8/1994 Johnson ........................ 606/235
5,354,274 A 10/1994 Demeter et al.
5,375,593 A 12/1994 Press
5,728,137 A 3/1998 Anderson-Fignon
5,948,003 A * 9/1999 Shefflin ........................ 606/234
6,126,678 A * 10/2000 Aaltonen et al. .............. 606/234
6,203,566 B1 3/2001 Alanen et al.
6,547,808 B2 4/2003 Tuckey et al.
6,905,507 B2 * 6/2005 Hinshaw ....................... 606/235
7,294,141 B2 * 11/2007 Bergersen ..................... 606/236
2003/0176891 A1 9/2003 Frederic

* cited by examiner

*Primary Examiner* — Tuan Nguyen

(57) ABSTRACT

The infant mouthpiece includes a U-shaped mouth mold for inserting into the mouth of the infant, wherein the mouth mold comprises a top, a bottom, a center, a distal end, a proximal end, and a plurality of ridges disposed along the top of the mouth mold. The infant mouthpiece further includes a female portion of a plug and a stopper, wherein the stopper comprises a proximal side, a distal side, and a center. The mouth mold, the stopper, and the female portion of the plug are connected such that the proximal end of the mouth mold is connected to the distal side of the stopper and the proximal side of the stopper is connected to the female portion of the plug.

8 Claims, 4 Drawing Sheets

BABY TEETHING/FEEDING DEVICE

FIELD OF THE INVENTION

The present invention is directed to an infant mouthpiece device for reducing pain during teething as well as for improved bottle feeding.

BACKGROUND OF THE INVENTION

There are currently many devices in use which serve as infant teethers and pacifiers. The present invention features an improved infant mouth piece for using during teething and/or during feeding. The infant mouth piece of the present invention may also be used as a pacifier.

The infant mouthpiece of the present invention comprises a U-shaped mouth mold for inserting into the mouth of the infant, wherein the mouth mold comprises a top, a bottom, a center, a distal end, a proximal end, and a plurality of ridges disposed along the top of the mouth mold. The U-shaped mouth mold maintains a continuous U-shape wherein the U-shaped mouth mold has an inside front wall 202. The inside front wall 202 positioned transverse to the top and the bottom. The mouth mold, the stopper, and the female portion of the plug are connected to the distal side of the stopper and the proximal side of the stopper is connected to the female portion of the plug. The infant mouthpiece further comprises a feeding hole having a first end 502 and a second end 504 wherein the first end of the feeder hole 502 opens to the female portion of the plug and the second end of the feeder hole 504 opens directly into the inside front wall of the mouth mold 202. The feeding hole is a hollow tubular channel from the center of the proximal portion of the mouth mold through the center of the stopper to the center of the female portion of the plug. The feeding hole is for allowing a liquid to travel from the female portion of the plug to the mouth mold, wherein the liquid may be swallowed by an infant.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF PREFERRED EMBODIMENTS

Figure 1:
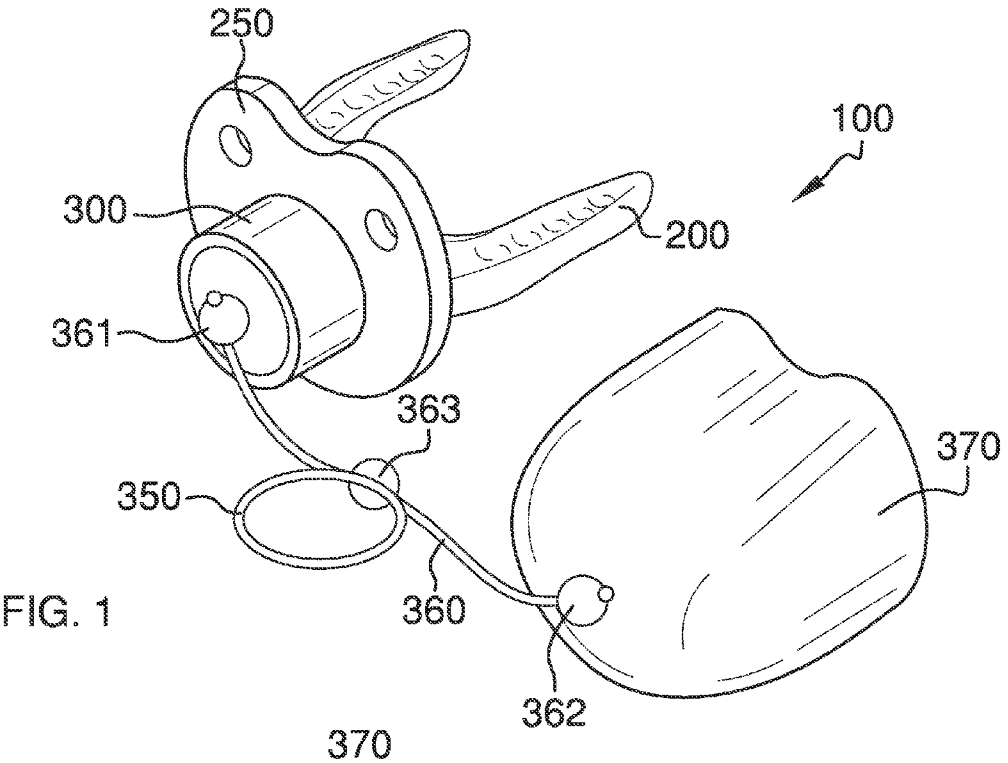
FIG. 1 is a perspective view of an infant mouthpiece 100 of the present invention.
Figure 2:
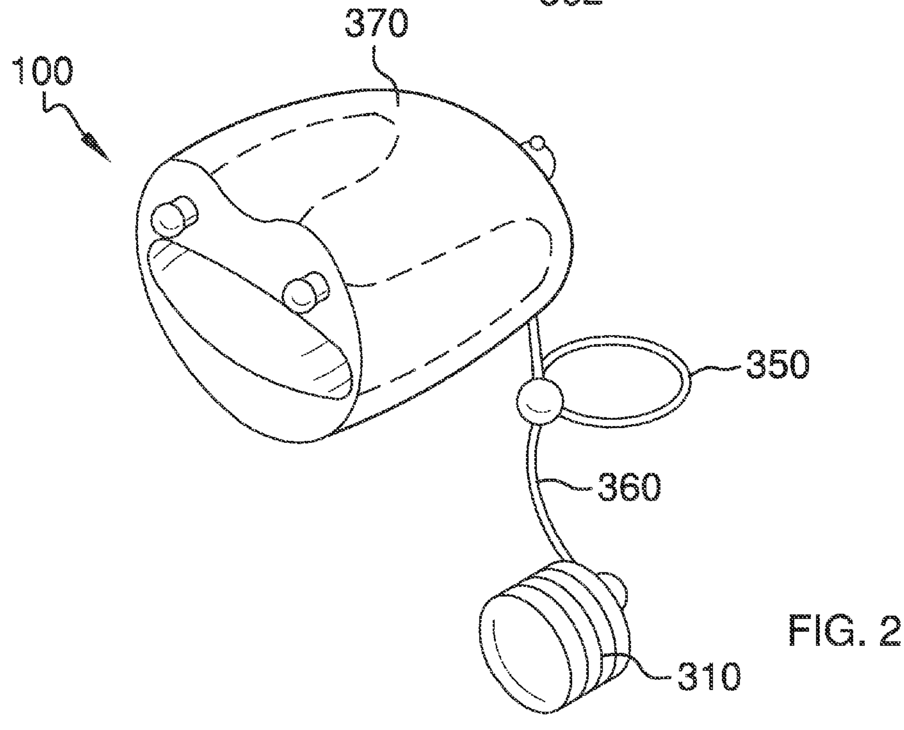
FIG. 2 is a perspective view of the infant mouthpiece 100 of FIG. 1 wherein the mouth mold 200 is inserted into a cap 370 attached to the cord 360.
Figure 3:
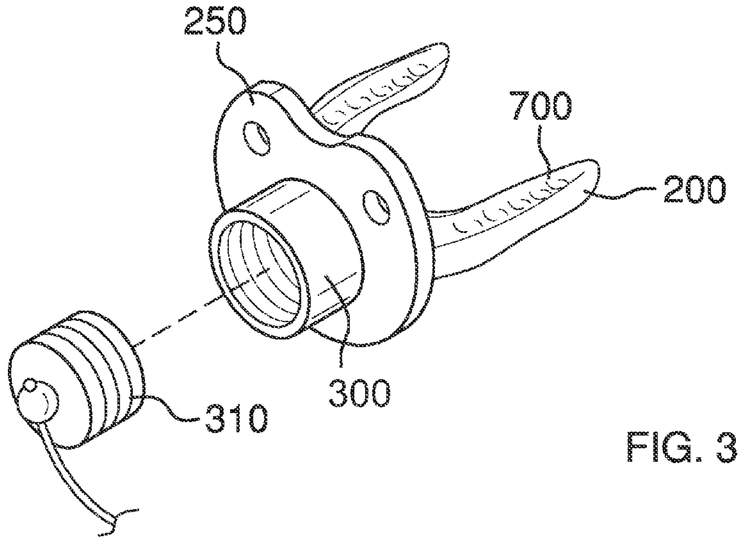
FIG. 3 is a perspective view of an infant mouthpiece 100 of the present invention.
Figure 4:
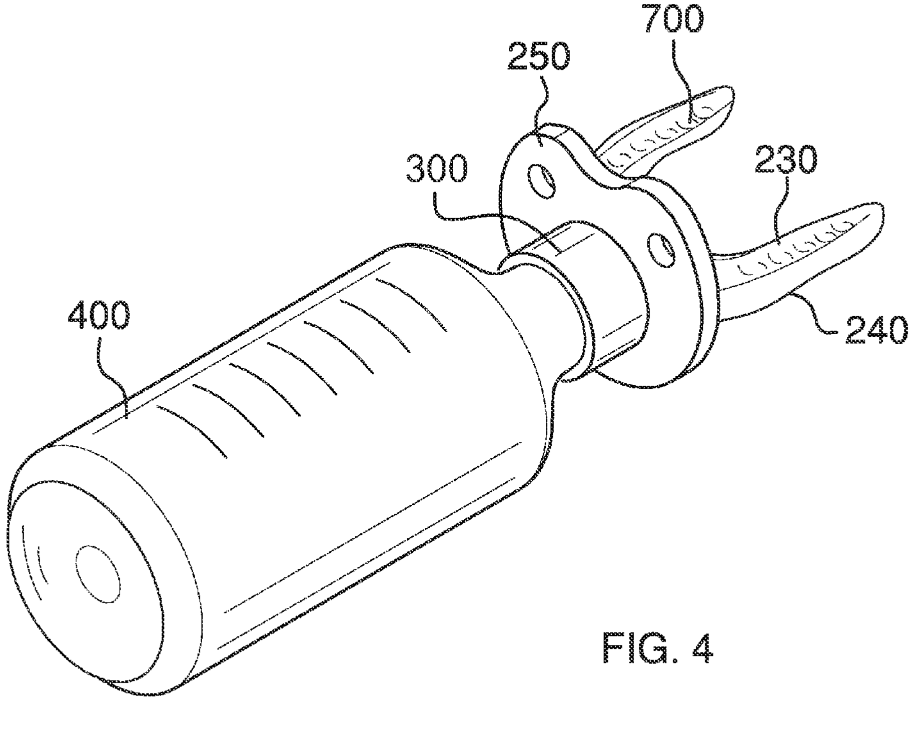
FIG. 4 is a perspective view of an infant mouthpiece 100 attached to a bottle 400.
Figure 5:
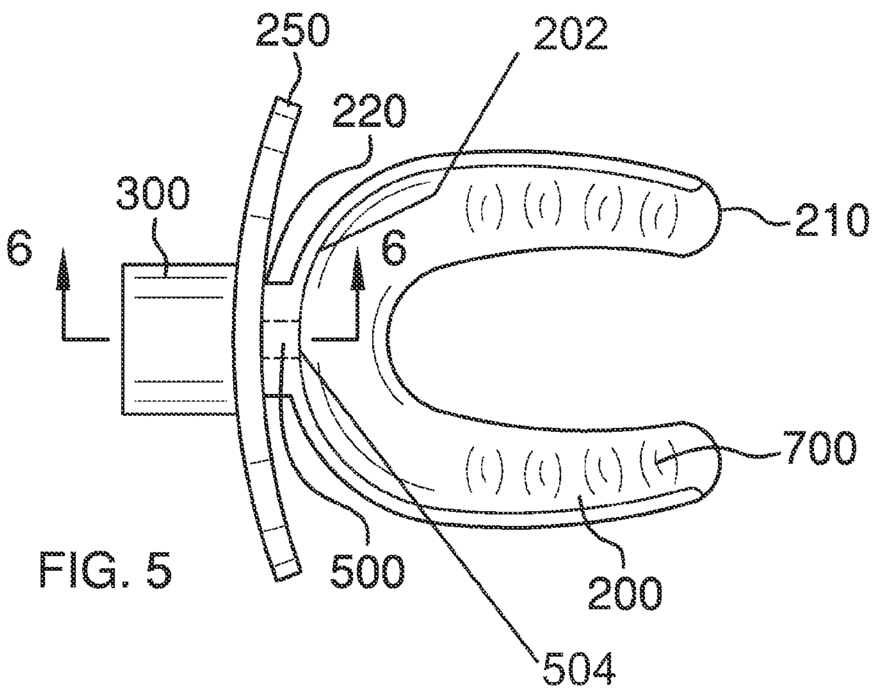
FIG. 5 is a top view of the infant mouthpiece of FIG. 1.
Figure 6:
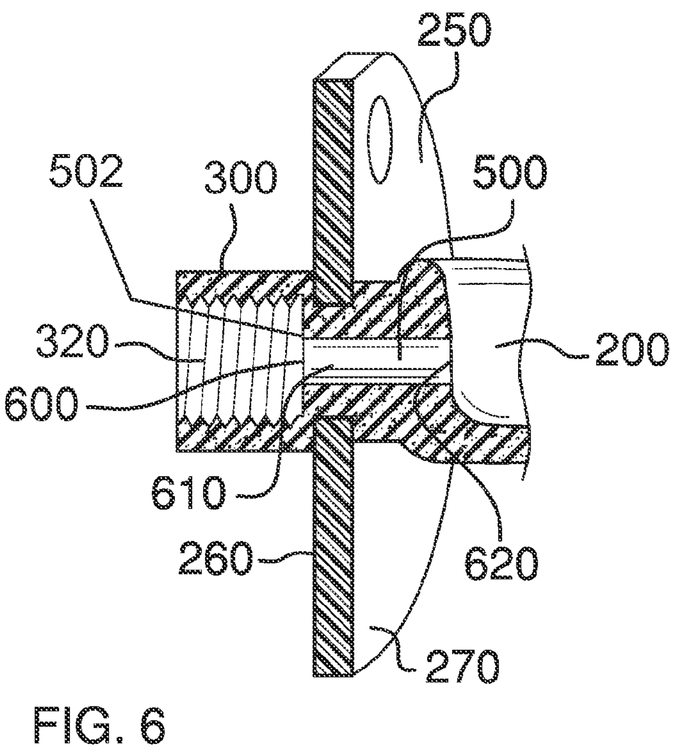
FIG. 6 is a cross section view of the mouthpiece of FIG. 5.
Figure 7:
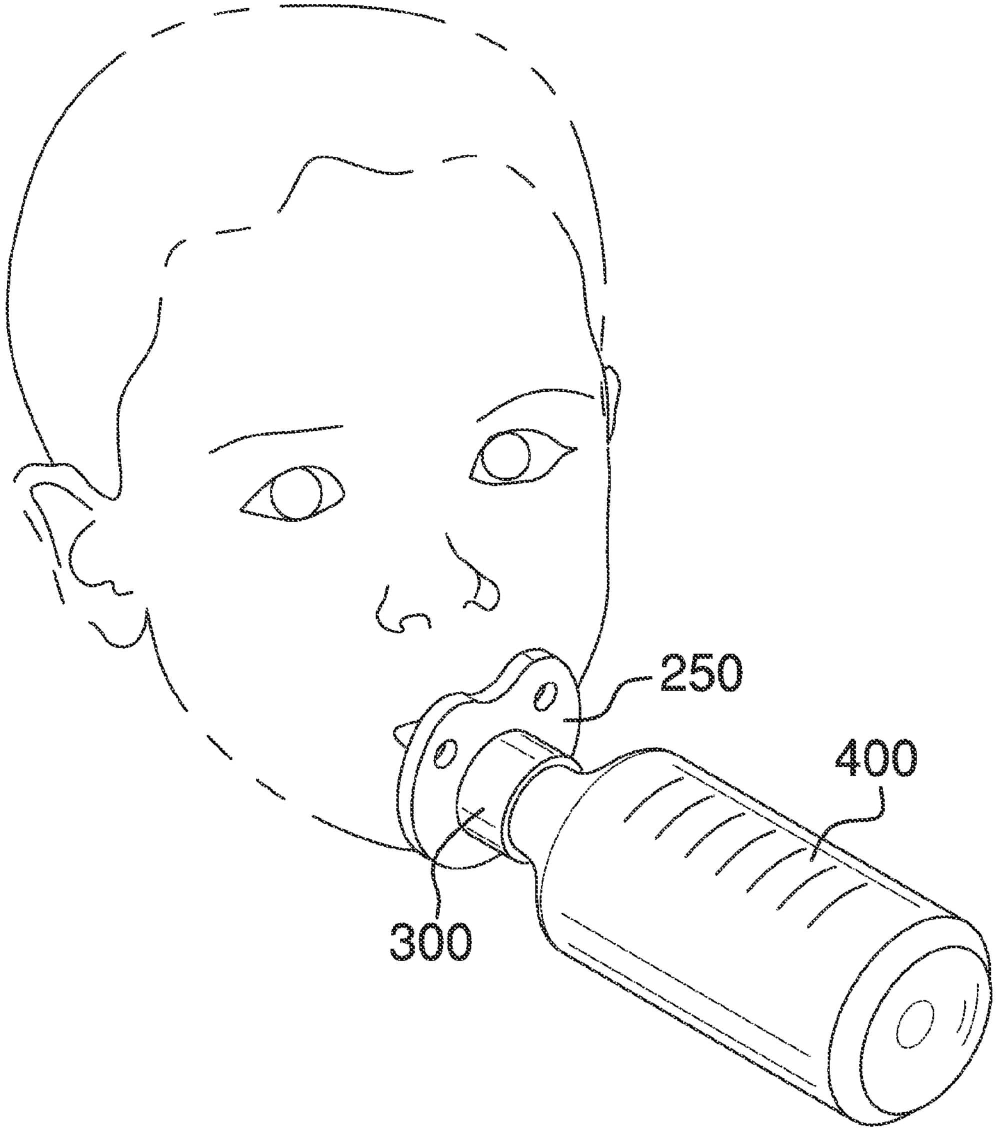
FIG. 7 is a perspective view of an infant using the infant mouthpiece 100 attached to a bottle 400 during feeding.

The following is a listing of numbers corresponding to a particular element refer to herein:

100 infant mouthpiece
200 mouth mold
210 distal end of mouth mold
220 proximal end of mouth mold
230 top of mouth mold
240 bottom of mouth mold
250 stopper
260 proximal side of stopper
270 distal side of stopper
300 plug
310 male portion of plug
320 female portion of plug
350 ring
360 cord
361 first end of cord
362 second end of cord
363 center of cord
370 cap
400 bottle
500 feeder hole
600 center of female portion of plug
610 center of stopper
620 center of mouth mold
700 indentation/ridge Referring now to FIGS. 1-7, the present invention features an infant mouthpiece, wherein the infant mouthpiece may be used for providing comfort to the infant during teething, for feeding the infant with a bottle, and/or as a pacifier. Without wishing to limit the present invention to any theory or mechanism, it is believed that the infant mouthpiece of the present invention reduces pain for a teething infant.

The infant mouthpiece of the present invention comprises a U-shaped mouth mold for inserting into the mouth of the infant, wherein the mouth mold comprises a top, a bottom, a center, a distal end, a proximal end, and a plurality of ridges disposed along the top of the mouth mold. The infant mouthpiece further comprises a female portion of a plug and a stopper, wherein the stopper comprises a proximal side, a distal side, and a center. The mouth mold, the stopper, and the female portion of the plug are connected such that the proximal end of the mouth mold is connected to the distal side of the stopper and the proximal side of the stopper is connected to the female portion of the plug. The infant mouthpiece further comprises a feeding hole, wherein the feeding hole is a hollow tubular channel from the center of the proximal portion of the mouth mold through the center of the stopper to the center of the female portion of the plug. The feeding hole is for allowing a liquid to travel from the female portion of the plug to the mouth mold, wherein the liquid may be swallowed by an infant.

In some embodiments, the infant mouthpiece further comprises a cord. In some embodiments, the cord comprises a first end, a second end, and a center. In some embodiments, a male portion of a plug is attached to the first end of the cord. In some embodiments, a ring is attached to the center of the cord. In some embodiments, a cap is attached to the second end of the cord. In some embodiments, the cap is for covering the mouth mold when the mouth mold is not in use. In some embodiments, the male portion of the plug is for inserting into the female portion of the plug, wherein the male portion of the plug is for closing the feeding hole.

In some embodiments, the mouth mold is non-permanently attached to the stopper. In, some embodiments, the mouth mold is permanently attached to the stopper. In some embodiments, the female portion of the plug is non-permanently attached to the stopper. In some embodiments, the female portion of the plug is permanently attached to the stopper.

In some embodiments, the male portion of the plug is inserted into the female portion of the plug for closing the feeding hole. Without wishing to limit the present invention to any theory or mechanism, it is believed that closing the feeding hole with the male portion of the plug will help prevent the infant from sucking in air while the mouth mold is inside his/her mouth. It may also prevent dirt, dust, and the like from entering into the feeding hole.

In some embodiments, the infant mouthpiece of the present invention may be used for feeding the infant with a bottle. In some embodiments, a bottle is screwed in to the female portion of the plug, wherein liquid from the bottle may travel through the feeding hole into the mouth of the infant.

In some embodiments, the infant mouthpiece of the present invention may be used for teething. Without wishing to limit the present invention to any theory or mechanism, it is believed that the mouth mold and the ridges disposed on the top of the mouth mold are soothing to an infant and will help to reduce pain during teething.

In some embodiments, the infant mouthpiece of the present invention may be used as a pacifier. In some embodiments, a nipple is screwed in to the female portion of the plug, wherein the infant may insert the nipple into his/her mouth. In some embodiments, the mouth mold is covered by a cap while the mouth mold is not in user.

In some embodiments, the infant mouth piece is used as a replacement bottle nipple.

As used herein, the term “about” refers to plus or minus 10% of the referenced number. For example, an infant mouthpiece that is about 1 inch wide includes an infant mouthpiece that is between 0.9 and 1.1 inches.

The infant mouth piece of the present invention may be constructed in a variety of sizes, designs, and with a variety of materials. In some embodiments, the infant mouthpiece of the present invention is constructed from a material comprising a plastic, a rubber, the like, or a combination thereof.

In some embodiments, the mouth mold is between about 1.0 and 2.0 inches long, as measured from the distal end to the proximal end. In some embodiments, the mouth mold is between 0.5 and 1.0 inches in height, as measured from the top to the bottom.

In some embodiments, the infant mouthpiece may be constructed for various infant ages and/or mouth sizes. For example, an infant mouthpiece may be constructed to suit an infant about 1 to 5 months old, about 6 to 12 months old, and/or about 12 to 18 months old.

In some embodiments, the distal end of the mouth mold is tapered, wherein the height of the mouth mold (as measured from the bottom to the top) at the distal end of the mouth mold is less than the height of the mouth mold at the proximal end.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. An infant mouthpiece for providing comfort to an infant during teething comprising:

(a) a U-shaped mouth mold, wherein the mouth mold comprises a top, a bottom, a center, a distal end, and a proximal end; wherein the month mold comprises a plurality of ridges disposed along the top of the mouth mold; wherein the mouth mold is for inserting into the mouth of the infant; wherein the U-shaped mouth mold maintains a continuous U-shape; wherein the U-shaped mouth mold further comprises an inside front wall disposed transverse to the top and the bottom;

(b) a stopper, wherein the stopper comprises a proximal side, a distal side, and a center;

(c) a female portion of a plug, wherein the female portion of the plug comprises a hollow center, wherein the mouth mold, the stopper, and the female portion of the plug are connected such that the proximal end of the mouth mold is connected to the distal side of the stopper and the proximal side of the stopper is connected to the female portion; and (d) a feeding hole, wherein the feeding hole is a hollow tubular channel from the center of the mouth mold through the center of the stopper to the hollow center of the female portion of the plug; wherein the feeding hole is for allowing a liquid to travel from the female portion of the plug to the U-shaped mouth mold; and wherein the feeding hole comprises a first end and a second end, wherein the first end of the feeding hole opens to the female portion of the plug and the second end of the feeding hole opens directly into the inside front wall of the mouth mold.

2. The infant mouth piece of claim 1, wherein, the infant mouthpiece further comprises a cord, wherein the cord comprises a first end, a second end, and a center.

3. The infant mouth piece of claim 2, wherein a male portion of a plug is attached to the first end of the cord, wherein the male portion of the plug is for inserting into the female portion of the plug, wherein the male portion of the plug is for closing the feeding hole.

4. The infant mouth piece of claim 2, wherein a ring is attached to the center of the cord.

5. The infant mouth piece of claim 2, wherein a cap is attached to the second end of the cord, wherein the cap is for covering the mouth mold when the mouth mold is not in use.

6. The infant mouthpiece of claim 1, wherein the infant mouth piece is used for feeding the infant with a bottle.

7. The infant mouthpiece of claim 1, wherein the infant mouthpiece is used as a pacifier.

8. The infant mouthpiece of claim 6, wherein a bottle is inserted into the female portion of the plug.

* * * * *